US00PP37395P2

(12) United States Plant Patent
Hansen

(10) Patent No.: US PP37,395 P2
(45) Date of Patent: Apr. 28, 2026

(54) ***HEMEROCALLIS* PLANT NAMED 'Honey Barbeque'**

(50) Latin Name: ***Hemerocallis* (L.) hybrid**
Varietal Denomination: Honey Barbeque

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,946

(22) Filed: Dec. 2, 2025

(51) Int. Cl.
*A01H 6/00* (2018.01)
*A01H 5/02* (2018.01)

(52) U.S. Cl.
USPC ..... Plt./312

(58) Field of Classification Search
USPC ..... Plt./312
CPC ..... A01H 6/00; A01H 5/02
See application file for complete search history.

*Primary Examiner* — Keith O. Robinson

(57) ABSTRACT

A new and distinct *Hemerocallis* plant named 'Honey Barbeque' characterized by winter-hardy compact habit with clean medium-green foliage that goes dormant in the winter. The flowers are rounded, fragrant, single, golden with a dark burgundy eye zone and gold throat. Tepals are slightly reflexed near apices lightly undulate on the margins. The new plant flowers on stems up to 39 cm tall with two to four-way branching beginning about early-June and repeating until frost.

2 Drawing Sheets

Botanical classification: *Hemerocallis* (L.) hybrid.
Variety denomination: 'Honey Barbeque'.

STATEMENT REGARDING PRIOR DISCLOSURES UNDER 37 CFR 1.77(B)(6)

The new cultivar was registered in 2025 with the American Daylily Society which is the International Cultivar Registration Authority for the genus *Hemerocallis* with a brief description and photograph. No plants of *Hemerocallis* 'Honey Barbeque' have been sold in this country or anywhere in the world, nor has any disclosure of the new plant been made more than one year prior to the filing date of this application and such sale or disclosure within one year was either derived directly or indirectly from the inventor.

BACKGROUND AND ORIGIN OF THE PLANT

The present invention relates to a new and distinct daylily plant, *Hemerocallis* 'Honey Barbeque' hereinafter also referred to as the new plant or just the cultivar name 'Honey Barbeque'. *Hemerocallis* 'Honey Barbeque' was hybridized on Jul. 10, 2013, in a trial garden at a wholesale perennial nursery in Zeeland, Michigan, USA. The female or seed parent was 'Black Eyed Stella' (not patented) and the male or pollen parent was 'Kokomo Sunset' (not patented).

The new plant was selected as a single seedling from this cross, and after confidential evaluations in a trial bed beginning in 2015 at the same nursery, the new plant was assigned the breeder code 13-5-3. The new plant has been asexually propagated by division at the same nursery in Zeeland, MI since 2015 with each of the resultant asexually propagated plants having retained all the same unique traits as the original plant in successive generations.

There are over 100,000 registered daylilies with The American *Hemerocallis* Society, which is the International Cultivar Registration Authority for the genus *Hemerocallis*.

The most similar daylilies known to the inventor are: 'Black Eyed Stella' (not patented), 'Black Eyed Susan' (not patented), 'Fancy Core' (not patented), 'Kokomo Sunset' (not patented), 'Orange Smoothie' U.S. Plant Pat. No. 28,643, and 'Small World Rock Candy' (not patented).

'Black Eyed Stella' has a shorter scape with slightly smaller flowers having golden tepals and a lighter orangish-red eye and gold throat, and the tepals are more pinched distally and more recurved. 'Black Eyed Susan' is a tetraploid, has taller scapes, more yellowish tepals with a more rusty reddish eye and golden yellow throat. 'Fancy Core' blooms a little later in the season on taller scapes with narrower tepals of golden orange and deep reddish eye. 'Kokomo Sunset' is a semi-evergreen tetraploid with shorter scapes of more golden-yellow with a lighter reddish eye and gold throat. 'Orange Smoothie' has taller scapes with more flowers per scape that have broader pastel-orange tepals with a deeper orange eye and large green throat with heavy undulation of the margin. 'Small World Rock Candy' has a taller scape with more flowers per scape and the tepals are a lighter yellow with a brighter red eye, and the tepal margin is more undulate with a picotee red edge around the proximal half.

*Hemerocallis* 'Honey Barbeque' differs from all other daylilies known to the applicant, by the combination of the following traits:

1. Winter-hardy, compact habit with clean medium-green foliage that goes dormant in the winter;
2. Fragrant, single, rounded flowers about 10.3 cm across of gold with a dark burgundy eye zone and gold throat;
3. Tepals slightly reflexed near apices and lightly undulate on the margins;
4. Plants produce two to four-way branched scapes of about 39 cm tall with up to 21 flowers per scape;
5. Flowering begins about early-June with excellent coverage and repeat flowering later in the season until frost.

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
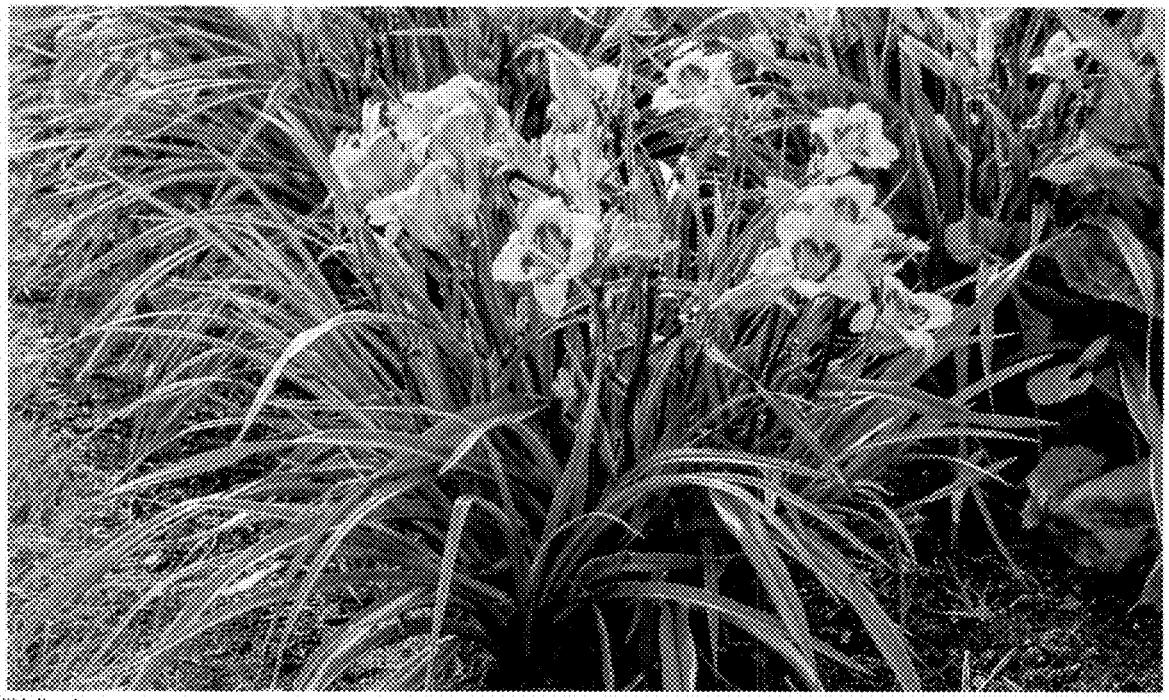
FIG. 1 shows a three-year-old plant in peak flower in a sunny trial garden during mid-summer in Zeeland, Michigan.
Figure 2:
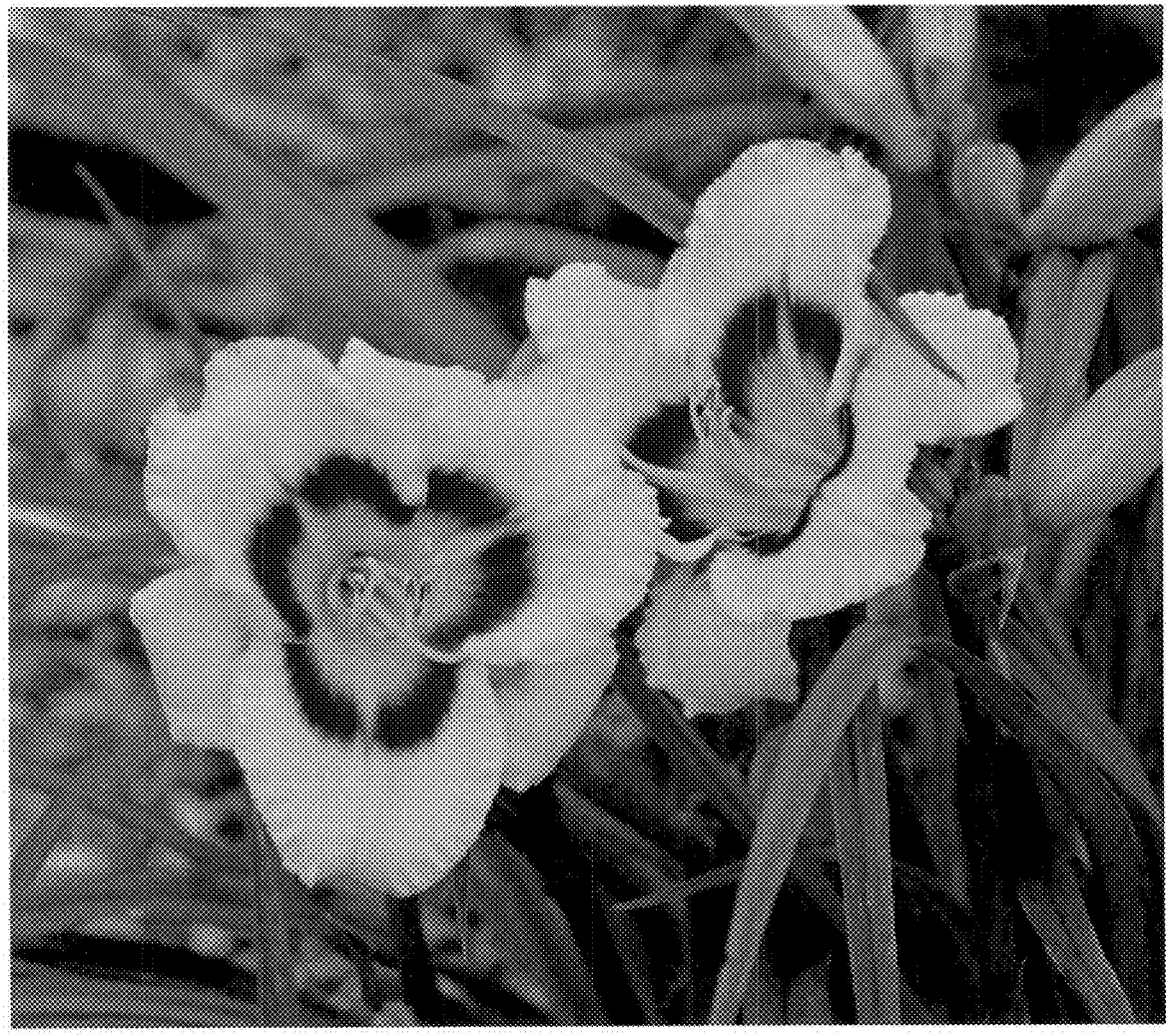
FIG. 2 shows a close-up of a flower and bud.

The following descriptions and color references are based on the 2015 edition of The Royal Horticultural Society Colour Chart except where common dictionary terms are used. The new plant, *Hemerocallis* 'Honey Barbeque', has not been observed under all possible environments. The phenotype may vary slightly with different environmental conditions, such as temperature, light, fertility, moisture and maturity levels, but without any change in the genotype. The following observations and size descriptions are of a three-year-old plant in a sunny landscape at a display garden in Zeeland, Michigan with supplemental water and fertilizer.

Botanical classification: *Hemerocallis* (L.) hybrid;

Parentage: Female (seed) parent is 'Black Eyed Stella'; male (pollen) is 'Kokomo Sunset';

Propagation: Division of the rhizome;

Growth rate: Moderate to rapid;

Crop time: About 8 to 10 weeks to flower starting in spring in a 3.8-liter container from vernalized one-year-old plant;

Rooting habit: Fleshy, about 2.5 mm diameter; lightly branching;

Root color: Nearest RHS 159C depending on soil type;

Plant shape and habit: Winter-hardy herbaceous perennial with about 12 basal shoots emerging from rhizomes producing a low radially-symmetrical mound of arching leaves;

Plant size: Foliage height about 45 cm tall from soil line to the top of the leaves and about 90 cm wide at the soil level;

Leaves: Entire; glabrous; slightly glaucous abaxial and adaxial; linear, sessile; folded; apex narrowly acute, base sheathing; to about 58 cm long and 20 mm across, average about 50 cm long and about 19 mm across; about 16 leaves per division;

Cauline leaves: 1 to 2 per scape; reduced, average about 12.5 cm long and 18 mm across;

Leaf color: Young adaxial between RHS 146B and RHS 146C, young abaxial between RHS 146C and RHS 146B; mature adaxial nearest RHS 137B, mature abaxial between RHS 146C and RHS 146B;

Veins: Parallel; color adaxial and abaxial nearest RHS 137B;

Flower description:

Flowers: Funnelform; single, with two sets of three tepals; zygomorphic, incomplete; up to 21 per scape, mostly distally arranged on 2 to 4 branches; upward and outwardly facing; about 10.3 cm across and 8 cm tall to exserted stigma, corolla about 6 cm deep; individually lasting for about one day; peduncle remains effective from mid-July into early-August for approximately three weeks in Zeeland, Michigan;

Flower fragrance: Not detected;

Buds one day prior to opening: Oblate ellipsoid with bluntly acute apex and tepals beginning to separate, and basal one-fifth narrowed terete; about 5.7 cm long and about 1.3 cm in diameter at widest point with basal one-fifth narrowing to about 7 mm diameter;

Bud color one day from opening: Apical 2 mm nearest RHS 146A, central portion between RHS 14C developing and RHS 15C, basal 15 mm nearest RHS 146C;

Tepals: 2 sets of 3;

Inner tepals: Ovate; glabrous; rounded apex; lightly crisped margins to about 1 mm deep; base truncate, fused in proximal 18 mm; width at fusion about 7 mm; midrib fluted about 2 mm wide on abaxial surface, flat adaxial center; reflexed about 60 to 90 degrees in distal one-eight; about 8.6 cm long and 4.2 cm across at widest point;

Outer tepals: Broadly lanceolate to elliptic; glabrous; acute apex; fused in proximal 18.mm; 2.8 cm across;

Inner tepal color adaxial: Center between RHS 17A and 17B with area around midrib nearest RHS 17B with an undertone of nearest RHS 146C, thin margin about 1 mm wide extending from about the middle of the tepal to two-thirds of the way to apex of nearest RHS 176A, with an eye zone between RHS 183A and RHS 183B, proximal portion about 2 to 2.5 cm wide nearest RHS 17A, midrib nearest RHS 17A;

Inner tepal color abaxial: Thin margin about 0.5 mm wide extending from about the middle of the tepal to two-thirds of the way to apex of nearest RHS 176A, and center nearest RHS 17A;

Outer tepal color adaxial: Center between RHS 17A and 17B, distally nearest RHS 17B, area around midrib nearest RHS 17B with an undertone of nearest RHS 146B, and eye zone about 5 mm thick of moderately blushed nearest RHS 176A;

Outer tepal color abaxial: Nearest RHS 17A, with the area around proximal midrib nearest RHS 17A with an undertone of nearest RHS 146C;

Pedicel: Cylindrical; glabrous; slightly lustrous; approximately 3 mm long, 3 mm diameter at base;

Pedicel color: Nearest RHS 144A;

Peduncle: Usually three per plant during peak initial flowering and two per plant with repeat flowering, erect to about 54.0 cm tall and 13 mm diameter at base, average 53 cm tall; extending above foliage; with 3 to 4 branches; branches to about 10 cm long and 6 mm diameter at base;

Peduncle and branch color: Nearest RHS NN137B in portions with direct sunlight and nearest RHS 144A in portions protected from direct sunlight;

Gynoecium: Single; tri-carpelled; glabrous; about 8 cm long;

*Style*.—Single; cylindrical; glabrous; slightly lustrous; about 7.2 cm long, 2 mm diameter, slightly arcuate upward at distal one-quarter; color between RHS 23C and RHS 23B.

*Stigma*.—Globose; puberulent; 1 mm tall to 2 mm diameter; color nearest RHS 18B.

*Ovary*.—Conical; smooth; acute apex, truncate base; about 7 mm long and 4 mm diameter at base; color between RHS 145B and RHS 145A.

Androecium: Six; glabrous;

*Filaments*.—Six; cylindrical; adnate to inner tepals in basal 22 mm above ovary; arcuate upward in distal 15 mm; free in distal 48 mm from fusion point on tepal; 63 mm long; slightly applanate proximally; 2.5 mm across and 2 mm thick; color nearest RHS 17B with a 8 mmm wide band on the adaxial side about 22 mm from base moderately to strongly blushed nearest RHS 176A.

*Anthers*.—Oblong; dorsifixed, longitudinal; about 10 mm long and 3.5 mm wide; color between RHS N77C and RHS 176C.

*Pollen*.—Elliptical; less than 0.1 mm long; color nearest RHS 14A.

Fruit: Oblong ellipse; non-fleshy, dehiscent, many-seeded, tri-loculicidal capsule; ellipse; about 2.4 cm long and 1.8 cm across; color while maturing nearest RHS 146C and at dehiscence between RHS 199A and RHS 199B;

Seed: About 3 to 6 per capsule; nearly-round dried berry; about 6 mm diameter; color nearest RHS 202A;

Ploidy: Presumed to be diploid but no scientific confirmation has been obtained;

Disease and pest resistance and tolerance: 'Honey Barbeque' has not shown resistance to diseases and pests beyond that common for daylilies, and due to the northern testing regions the new plant has not been fully exposed to daylily rust, *Puccinia hemerocallidis*.

Culture: The plant grows best and shows best coloration with plenty of moisture, adequate drainage and light shade during the hottest period of the day, but is able to tolerate some drought when mature and direct sun without leaf burn when provided sufficient water.

Hardiness at least from USDA zone 3 through 9.

The new plant is useful for landscaping en masse, as a single specimen, or small groups.

I claim:

1. A new and distinct ornamental daylily plant cultivar named *Hemerocallis* 'Honey Barbeque' as herein described and illustrated.

* * * * *